United States Patent
Yang et al.

(10) Patent No.: US 10,991,133 B2
(45) Date of Patent: Apr. 27, 2021

(54) VOLUME RENDERING FROM THREE-DIMENSIONAL MEDICAL DATA USING QUANTUM COMPUTING

(71) Applicant: Siemens Healthcare GmbH, Erlangen (DE)

(72) Inventors: Lining Yang, East Windsor, NJ (US); Christoph Vetter, Hopewell, NJ (US); Feng Qiu, Pennington, NJ (US)

(73) Assignee: Siemens Healthcare GmbH, Erlangen (DE)

(*) Notice: Subject to any disclaimer, the term of this patent is extended or adjusted under 35 U.S.C. 154(b) by 50 days.

(21) Appl. No.: 16/257,590

(22) Filed: Jan. 25, 2019

(65) Prior Publication Data

US 2020/0242816 A1    Jul. 30, 2020

(51) Int. Cl.
  G06T 11/00    (2006.01)
  G16H 30/40    (2018.01)
  G06T 15/08    (2011.01)
  G06N 10/00    (2019.01)

(52) U.S. Cl.
  CPC ............ G06T 11/008 (2013.01); G06N 10/00 (2019.01); G06T 15/08 (2013.01); G16H 30/40 (2018.01)

(58) Field of Classification Search
  None
  See application file for complete search history.

(56) References Cited

U.S. PATENT DOCUMENTS

| | | | |
|---|---|---|---|
| 9,237,849 B1* | 1/2016 | McKenzie | A61B 5/0033 |
| 10,007,885 B1* | 6/2018 | Gorshkov | G01N 29/4472 |
| 10,255,696 B2* | 4/2019 | Wang | G06T 11/006 |
| 10,339,634 B2* | 7/2019 | Wang | G06T 11/006 |
| 10,354,377 B2* | 7/2019 | Tan | G06T 15/06 |
| 10,388,020 B2* | 8/2019 | Guo | G06T 7/143 |
| 10,885,678 B2* | 1/2021 | Bishop | G06N 10/00 |
| 2006/0193510 A1* | 8/2006 | Matsumoto | G06T 15/06 382/154 |
| 2009/0167763 A1* | 7/2009 | Waechter | G06T 17/005 345/426 |
| 2015/0078640 A1* | 3/2015 | Guo | G06T 7/11 382/131 |
| 2015/0078641 A1* | 3/2015 | Tan | G06T 7/12 382/131 |
| 2016/0350960 A1* | 12/2016 | Yi | G06T 15/06 |
| 2019/0220782 A1* | 7/2019 | Chen | G06N 5/003 |

OTHER PUBLICATIONS

S. Caraiman and V. Manta, "Image processing using quantum computing," 2012 16th International Conference on System Theory, Control and Computing (ICSTCC), Sinaia, 2012, pp. 1-6. (Year: 2012).*

(Continued)

*Primary Examiner* — James A Thompson

(57) ABSTRACT

To reduce complexity and corresponding run time, quantum computation is used for rendering a volume. The quantum computation may search for voxels along a ray or the minimum or maximum. The quantum computation may orient (e.g., rotate) data for more efficient searching for the maximum or minimum. Due to the superposition in quantum computing, the efficiency in volume rendering medical images is increased as compared to traditional binary approaches.

18 Claims, 1 Drawing Sheet

(56) References Cited

OTHER PUBLICATIONS

"Lecture 4: Grover's Algorithm." Quantum Computation (Sep. 21, 2015). pp. 1-12.
Boyer, Michel, et al. "Tight bounds on quantum searching." Fortschritte der Physik: Progress of Physics 46.4-5 (1996): pp. 1-8.
Brassard, Gilles, et al. "Quantum amplitude amplification and estimation, 2000." pp. 1-32.
Durr, Christoph, and Peter Hoyer. "A quantum algorithm for finding the minimum." arXiv preprint quant-ph/9607014 (1996). pp. 1-2.
Marco Lanzargorta, et al. "Quantum Computer Science." Synthesis Lectures On Quantum Computing #2. (2009). pp. 1-125.
Wallis, Jerold W., et al. "Three-dimensional display in nuclear medicine." IEEE Transactions on Medical Imaging 8.4 (1989): 297-230.
Yan, Fei, et al. "Quantum image rotation by an arbitrary angle." Quantum Information Processing 16.11 (Apr. 2017): pp. 1-21.

* cited by examiner

VOLUME RENDERING FROM THREE-DIMENSIONAL MEDICAL DATA USING QUANTUM COMPUTING

BACKGROUND

The present embodiments relate to rendering in medical imaging. For three-dimensional visualization, different rendering approaches provide different information to assist the physician in diagnosis or treatment. Two common approaches are the volume rendering technique (VRT) mode and the maximum intensity projection (MIP) mode.

In traditional volume rendering (e.g., VRT by ray cast or other object-oriented techniques), each pixel of the final image is sampled along the viewing direction as a direct function of collected samples within the viewing volume. In VRT, each image sample on the viewing direction of one pixel is classified as a color sample then composited to the final image.

In MIP, the sample with the maximum or minimum value along a view ray is assigned to one pixel of the final image. Maximum intensity projection is typically run as a ray casting algorithm, where for each pixel of the display device, a ray is cast into the volumetric data, and the maximum value along the ray is selected. MIP is commonly used in angiography to extract vascular structures from medical computed tomography (CT) or magnetic resonance imaging (MRI) datasets. Minimum intensity Projection (MinIP) may be used to extract the low-intensity structures from volume data. The lowest data value encountered along each viewing ray is determined. MinIP is often used for examining lungs or airways.

MIP and MinIP are complementary methods from an algorithmic point of view. By reversing the maximum and minimum, these algorithms are mirror symmetric. MIP and MinIP are intrinsically computationally expensive because the algorithm must visit all voxels along each viewing ray to find the maximum or minimum value. Common volume rendering acceleration techniques such as space leaping and early ray termination cannot be applied. Although some optimization can be used to speed up MIP or MinIP, the overall complexity for rendering a MIP or MinIP is still O(N) where N is the number of voxels in the volume. The run time for each ray is bounded by the volume dimensions and therefore is O(N).

SUMMARY

By way of introduction, the preferred embodiments described below include methods, systems, instructions, and computer readable media for rendering in medical imaging. To reduce complexity and corresponding run time, quantum computation is used for rendering a volume. The quantum computation may search for voxels along a ray or the minimum or maximum. The quantum computation may orient (e.g., rotate) data for more efficient searching for the maximum or minimum. Due to the superposition in quantum computing, the efficiency in volume rendering medical images is increased as compared to traditional binary approaches.

In a first aspect, a method is provided for volume rendering in medical imaging. A volume of a patient is scanned with a medical scanner. The scanning providing intensities representing the volume. The measured amplitudes of signals provide the intensities. A quantum computer renders a maximum or minimum intensity projection of the intensities representing the volume to a plane with quantum computation. An image of the maximum or minimum intensity projection is displayed, such as on a display screen. The image represents the patient.

The scanning may be by computed tomography, positron emission tomography, single photon emission computed tomography, x-rays, magnetic resonance, or ultrasound. By scanning the volume, the intensities represent a three-dimensional distribution of locations in the volume. The image is a two-dimensional distribution of pixels rendered from the three-dimensional distribution.

For a maximum intensity projection, the pixels values each are a maximum along a ray from the pixel. For a minimum intensity projection, the pixels values each are a minimum along a ray from the pixel.

In one embodiment, the quantum computation is a quantum algorithm using qubits with initialized values and measurement of a collapsed state of the qubits of the quantum computer.

In one embodiment, a quantum search algorithm is used in rendering. For example, the quantum search algorithm searches for intensities representing the volume along each of different lines. As another example, the quantum search algorithm searches for a minimum or maximum of the intensities representing the volume along each of different lines. A combination of quantum computations may be used, such as rendering by: creating uniform superposition states representing positions of the intensities for the volume; counting, by quantum amplitude amplification and estimation, voxels intersecting a ray from a pixel; identifying, by quantum searching, the voxels intersecting the ray based on solutions initialized by the counting; creating a superposition of the intensities of the identified voxels; and determining, by quantum finding, the minimum or maximum of the intensities of the identified voxels. This combination provides rendering with a complexity of $O(\sqrt{N})$ per pixel where N is a number of voxels in the volume.

In another embodiment, the quantum computation rotates slices of the intensities representing the volume to be parallel with an image plane in the rendering. The rendering may further determine a maximum or minimum one of the intensities for each pixel of the image plane by comparison of the intensities of each rotated slice to buffered pixel values. This combination of quantum computing and comparison to buffered values renders with a complexity of $O(N*\ln M*\ln P)$ where N, M, and P are numbers of voxels along each spatial dimension of the volume.

In another aspect, a method is provided for volume rendering in medical imaging. A volume of a patient is scanned with a medical scanner. The scanning provides intensities representing the volume. A quantum computer volume renders an image of the patient from the intensities representing the volume with quantum computation. The volume rendered image of the patient is displayed, such as on a display screen.

The volume rendering may be any one of various types, such as a minimum or maximum intensity projection as the image.

In one embodiment, the volume rendering with quantum computation includes counting a number of the intensities along a ray with the quantum computation, identifying the intensities along the ray with the quantum computation, and/or determining a pixel value from the intensities along the ray with the quantum computation. In another embodiment, the volume rendering includes rotating slices of the intensities of the volume with the quantum computation.

In a third aspect, a system is provided for volume rendering in medical imaging. A medical imaging system is configured to scan an internal region of a patient and generate voxel data representing a volume of the internal region. A quantum computer is configured to contribute to rendering an image of the internal region from the voxel data with quantum computation. A display is configured to display the image of the internal region.

In one embodiment, the quantum computer is configured to render the image as a minimum or maximum intensity projection.

In other aspects, the acts of the methods are provided as instructions stored in a non-transitory computer readable medium. A quantum computer and/or other processor executing the instructions causes performance of the acts. A computer product with the instructions may be provided. Any of the characterizations in one type of aspect (e.g., method, system, computer readable medium, or computer product) may be used in other aspects.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Instead of using a bit to represent 0 or 1 as done by classical or binary computers, quantum computers use qubits where a qubit may represent a mixture or superposition of the 0 and 1 states. In another words, the state of a qubit may be represented as a linear combination of the 0 state and the 1 state. Quantum computing is a probabilistic computation model that operates in a computation space that is exponentially larger than what is possible with classical registers and offers intrinsic parallelism. These properties of quantum computing support algorithm solutions to be more efficient than what is possible with classical algorithms using binary.

Quantum computing algorithms may generate volume renderings in medical imaging more efficiently or with less complexity or number of operations than classical computing. For example, quantum computation is used for rendering MIP or MinIP images faster than classical algorithms. MIP or MinIP images are generated from volumetric datasets using a quantum computing algorithm. Various quantum computations may be used. Example approaches and corresponding algorithms using Quantum Computing concepts to compute MIP and MinIP images from 3D volumes are provided below. Other quantum computations or a combination of both may be used. Because of the intrinsic parallelism with quantum computing, extending quantum algorithms to calculate MIP or MinIP images from volume data achieves better performance compared to the classical algorithm. The processing may occur more rapidly, resulting in production of a volume rendered image from a large medical volume data set more quickly than classical computing.

Figure 1:
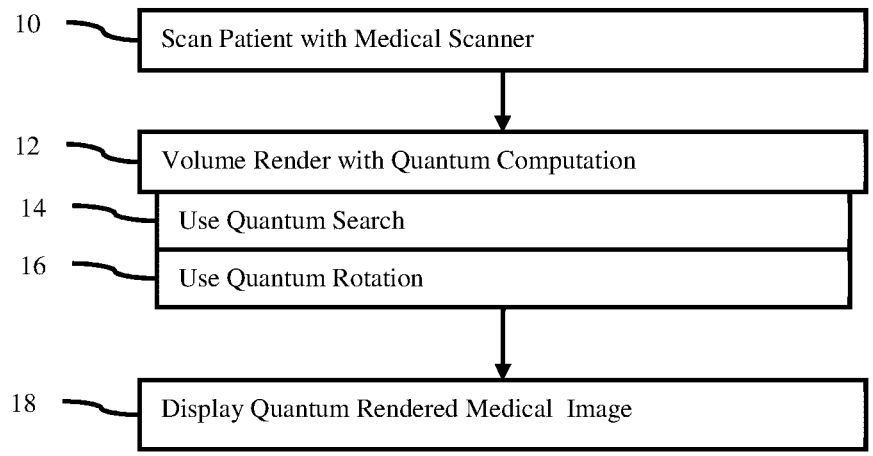
FIG. 1 is a flow chart diagram of one embodiment of a method for volume rendering with quantum computation in medical imaging.

FIG. 1 shows a method for volume rendering in medical imaging. Quantum computation is used to render an image from a scan volume. A quantum computer provides for at least part of the rendering of a volume to a 2D image. MIP and MinIP are used as examples, but VRT, alpha blending, projection, or another type of rendering may use quantum computation for medical imaging rendering.

Figure 2:
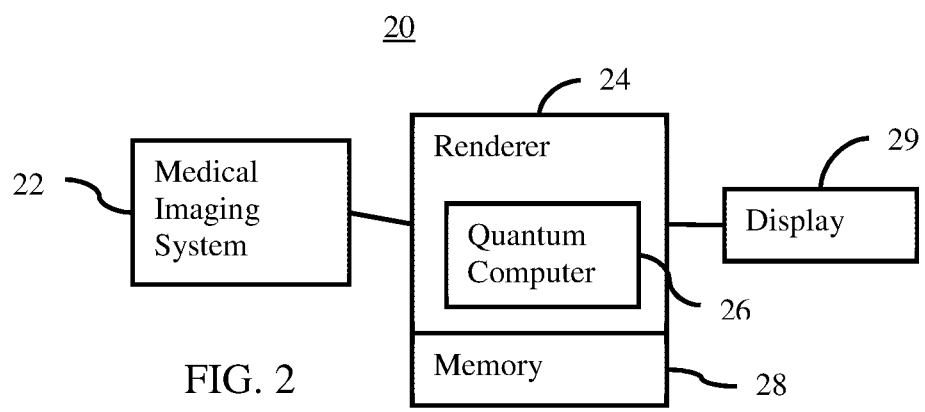
FIG. 2 is a block diagram of one embodiment of a system for volume rendering with a quantum computer in medical imaging.

The method is implemented by the system 20 of FIG. 2 or another system. For example, act 10 is performed by a medical scanner, acts 12-16 are performed with a quantum computer with or without another type of computer or processor, such as a processor operating using binary coding. Acts 12-16 may be performed with a quantum computer as part of a renderer operating with qubits or both qubits and binary registers. Act 18 is performed by the quantum computer or other type of computer using a display device or screen and a display buffer. Any one or more of the acts may be performed by different devices.

The acts are performed in the order shown or other orders. For example, acts 14 and/or 16 are performed as part of act 12.

Additional, different, or fewer acts may be provided. For example, acts for user interaction with rendered images and/or control of the viewing direction or other rendering are provided. As another example, user configuration for the scanning is provided. In yet another example, acts 14 and/or 16, related to specific quantum computation algorithms, are optional. In another example, act 10 is not performed as the scan data is instead loaded from a memory.

In act 10, a medical scanner acquires a set of voxels. The set represents a volume of the patient. A volume of a patient is scanned with the medical scanner. An interior region of the patient is scanned, such as with magnetic resonance (MR), x-ray (e.g., CT), ultrasound, or emission tomography (e.g., PET or SPECT). The scan is performed in any format, such as detecting emissions along lines of response, acquiring k-space data at magnetic gradient defined locations, or acquiring projections through the patient with x-rays from different directions.

A renderer or the medical imaging system reconstructs a volume representing, at least in part, the internal portion of the patient. Any reconstruction from the scan data may be used. Tomography or other process may be used to determine intensities for different locations distributed in three dimensions. As a result of the scan, data representing the interior of the patient in an N×M×O region or volume is acquired, where N, M, and O are integers greater than 1. The reconstruction determines scalar values or intensities for each of a plurality of voxels distributed in three dimensions.

In alternative embodiments, the intensities are classified as color. For example, a classification or transform function is applied to convert the measured amplitudes to red, green, blue, opacity (RGBα) or color values as the intensities. The color values are used as the intensities.

The intensities are scalar values representing the amplitude, power, energy, or other characterization of the measurement by location of the patient. The intensities represent response from blood, tissue, bone, other object, and/or contrast agents in the patient. In one embodiment, the voxel data is computed tomography data representing a cardiovascular system or blood or contrast agent in vessels and/or the heart of the patient. Other information may be included, such as response from tissue.

In act 12, a renderer renders an image from the intensities representing the volume of the patient. The three-dimensional distribution of voxels or intensities is rendered to a two-dimensional image for display. The intensities are transformed to pixel values in a two-dimensional distribution based on a view direction. The pixel values of the two-dimensional image are determined from the voxel values of the three-dimensional distribution. The pixels values may then be used on the two-dimensional screen or display. The image is rendered to the display but may be rendered and provided to a memory or network.

The renderer includes a quantum computer. Any quantum computer, such as a noisy intermediate-scale quantum (NISQ) device, may be used. The quantum computer operates with qubits using quantum-mechanical phenomena, such as superposition and/or entanglement. The qubits may be in a superposition of states. Based on initialization of the qubits, a quantum algorithm and/or computation based on quantum logic gates and collapsing the superposition into measured results setting the observed state, the quantum computer provides one of the eigenstates of the superposition as the result. The quantum computer may provide the solution as the result with a known probability of accuracy. Any number of intermediate results may be found using quantum computation. As a final result of the quantum algorithm, the quantum computations of the algorithm may be repeated any number of times (e.g., 4 times) to confirm or select a most likely state. Alternatively, the quantum algorithm is performed once where the known probability is above a threshold level.

The renderer may or may not also include a classical computer or processor (i.e., processor operating in a non-quantum computational way, such as operating with transistors having binary states without superposition). The renderer may include the quantum computer for some actions and a classical computer for other actions. Alternatively, the quantum computer performs all the rendering acts.

The rendered image is a volume rendered image. For example, a MIP image is rendered, providing a 2D distribution of pixel values. As another example, a MinIP image is rendered. The rendered image represents the interior region of the patient as viewed from a given direction on a 2D display screen. A projection of the 3D intensities representing the volume to a plane is generated, at least in part, with quantum computation. For MIP, the maximum intensity projection along each ray from each pixel through the voxels or volume provides the corresponding pixel value. For MinIP, the minimum intensity projection is used.

Any quantum computation may be used. A quantum algorithm uses qubits with initialized values and measurement of a collapsed state of the qubits of the quantum computer. Any part of rendering may use the quantum computation. For example, in act 14, a quantum search algorithm is used to search for voxels intersecting rays and/or to search for the maximum or minimum along a ray to be the pixel value. As another example, the quantum computation is used to count a number of the intensities along a ray, identify the intensities along the ray, and/or determine a pixel value from the intensities along the ray.

The MIP and MinIP algorithm is by nature a search problem, thus it is a good candidate for optimization using Grover's quantum search or another quantum search algorithm. MIP or MinIP may be implemented by executing a quantum search for the intersections between rays and voxels and/or a quantum search for the voxels that have the maximum or minimum value for each different ray.

In one embodiment, an algorithm or program for MIP or MinIP rendering includes various quantum calculations. The number of voxels is N (or $n^3$ for n being equal width, height, depth). The program determines the pixel value (e.g., intensity) for each pixel in a 2D image (i.e., pixels in x, y space). To initialize one quantum computation, values are provided to the qubits, creating uniform superposition states representing positions of the intensities for the volume. The qubits represent superposition states representing all the possible voxel positions. Quantum amplitude amplification and estimation or other quantum algorithm counts the number of voxels intersecting a ray from a pixel. Quantum amplitude amplification and estimation provides an algorithm that performs approximate counting of the elements in an unordered array that fulfill a specific condition—along a ray. This count c of voxels that intersect the ray from the pixel has a complexity of $O(\sqrt{N/c})$, where N is the number of voxels in the volume. The counting is used to initialize solutions for a search of the voxels intersecting the ray. Quantum searching is used to identify the voxels intersecting the ray based on solutions initialized by the counting. For example, a tight bounds on quantum searching algorithm searches the c elements fulfilling a condition (intersecting the ray) in an unordered array of the N voxels. The complexity of the search is $O(\sqrt{N/c})$. The next search is initialized by creating a superposition of the intensities of the identified voxel values for the voxels along the ray for the pixel. Quantum searching or finding is used to determine the minimum or maximum of the intensities of the identified voxels along the ray. For example, a quantum algorithm for finding the minimum determines the minimum element (intensity) of an unsorted array of V elements with complexity $0(\sqrt{V})$. The maximum may be found by exchanging the comparison operator.

In this embodiment, the overall rendering complexity is in the order of $O(\sqrt{N})$ per pixel where N is a number of voxels in the volume. Other complexities may be provided. The complexity is less than the MIP or MinIP algorithms using binary states in classical computing.

Quantum searching may be used with volumes or voxel arrangements on a regular or irregular grid or formed from a point cloud. Most CT or MR scans produce datasets on a regular grid such that the volume is formed from a stack of planes or slices of voxels with a one voxel depth. The quantum searching may not take advantage of this regular grid.

In another embodiment, the regular grid is used in the quantum computation. In this embodiment, in act 16, the quantum computation rotates the volume or slices making up the volume based on the view direction. The intensities, such as planar slices or layers of intensities forming the volume, are rotated by quantum computation to be parallel to the view or image plane defined by the viewing direction in rendering. Quantum computation in a quantum algorithm may be used to perform image rotation by an arbitrary angle through several shear transformations. The shear transformations linearly displace each pixel in the slice towards a fixed direction to its signed distance according to the shear factor. These operations are further decomposed into addition, self-addition, multiplication and interpolation operations that are performed with corresponding quantum circuits. For an arbitrary viewing angle, each slice of the volume is projected to the viewing plane through an image rotation.

After rotation of each slice, a maximum or minimum one of the intensities for each pixel of the image plane is determined by comparison of the intensities of each rotated slice to buffered pixel values. After rotation of each slice, the resulting image or intensities of the slice as rotated are compared to the existing values in the resulting image (i.e., buffered pixel values) to determine the max or min values. For MIP, if the slice value for the projected pixel is greater than the current pixel or buffered value, then the pixel value is replaced by the projected pixel from the slice. This is done for all the slices to achieve the final image.

The comparison to determine the maximum uses binary programming with a classic computer. Alternatively, the slices are rotated, and a quantum search is used to find the maximum or minimum for each pixel from the quantum rotated slices.

An image rotation by an arbitrary angle may be achieved for an image of M*P dimension with complexity in the order of $O(\ln M * \ln P)$. Therefore, the complexity for a Q*M*P volume is in the order of $O(Q*\ln M*\ln P)$. Q, M, and P are numbers of voxels along each spatial dimension of the volume as rotated to the viewing plane.

Other quantum computation may be used in rendering. Any of the rendering acts may use the quantum computer, such as searching, rotating, transformation, interpolation, or projection.

In act 18, the volume rendered image is transmitted. The transmission is to a display, such as a display buffer. The output of the display buffer to the display generates the image for viewing on a display screen. The rendered image or images are displayed by the renderer on the display. The image represents the patient, such as an interior region of the patient viewed from a given direction. Alternatively, the image is transmitted to a network or memory, such as a picture archiving communications system.

The rendered image is a MIP or MinIP image representing the maximum or minimum intensity along each ray from each pixel through the volume. The rendered image may use other transform functions, such as alpha blending or other VRT transform functions to relate the values along the ray to the pixel value for each pixel.

FIG. 2 shows one embodiment of a system 20 for volume rendering in medical imaging. The system 20 renders a volume of a patient for medical visualization. MIP, MinIP, VRT, or other rendering from a 3D scan of a patient is provided. Quantum computation using a quantum computer 26 performs at least part of the rendering, such as the search, rotation, transfer function, classification, windowing, and/or other rendering operation.

The system 20 includes a medical imaging system 22, a renderer 24, a memory 28, and a display 29. Additional, different, or fewer components may be provided. For example, a network or network connection is provided, such as for networking with a medical imaging network or data archival system. As another example, a user interface is provided for configuring the rendering, such as providing a point of view or viewing direction.

The renderer 24, memory 28, and display 29 are part of the medical imaging system 22. Alternatively, the renderer 24, memory 28, and/or display 29 are part of an archival and/or image processing system, such as associated with a medical records database workstation or server. In other embodiments, the renderer 24, memory 28, and/or display 29 are a separate computer, such as desktop or laptop, a workstation, a server, or combinations thereof. The renderer 24, memory 28, and display 29 may be parts of different systems, such as the memory 28 being in a picture archiving and communications system (PACS), the renderer 24 being part of a workstation, and/or the display 29 being an imaging system or radiological display.

The system 20 is configured to implement the method of FIG. 1. Alternatively, other methods are implemented.

Any medical imaging system 22 may be used. For example, the medical imaging system 22 is a CT, MR, ultrasound, x-ray, fluoroscopy, optical coherence tomography, or emission tomography (i.e., functional imaging such as PET or SPECT) system. The medical imaging system 22 is any now known or later developed medical imaging system for scanning an interior of the patient. The medical imaging system 22 is configured by hardware, firmware, and/or software to scan the internal region of a patient and generate voxel data representing a scanned volume of the internal region.

The medical imaging system 22 is configured to scan an internal region of the patient. The surface or skin of the patient may or may not also be scanned. Any portion or extent of the patient may be scanned, such as a scan of an organ, torso, extremity, or full body. The scan acquires data representing the interior of the patient. The represented portion includes a volume or three-dimensional distribution of response from the patient.

The medical imaging system 22 is configured to scan the patient to acquire at least one set of data. The set or frame of voxel data represents the internal region of the patient at a specific time or period. A static volume is acquired. Alternatively, the scanning is repeated or performed in an ongoing manner to acquire a sequence of sets of voxel data. Each set represents the volume at a given time or period, so the sequence represents the volume over time (3D+t or 4D data). Any frame or volume rate may be provided. For real-time rates, at least 10 volumes or sets of voxel data are acquired each second. Greater or lesser volume rates may be provided.

The scan data may be output as a 3D reconstruction or data representing a volume. Alternatively, the acquired scan data is reconstructed to represent the volume. For example, Fourier processing is applied to k-space data in MR to reconstruct the volume. As another example, computed tomography is used to reconstruct the volume (e.g., SPECT or CT). In yet another example, data representing three dimensions in a scan format is interpolated to a regular or other grid, such as a Cartesian coordinate grid. Each datum is associated with a different volume location (voxel) in the patient volume and assigned a scalar intensity.

The data from the scan is formatted as voxels in an isotropic grid. For example, voxels in a 512×512×512 Cartesian grid are used. Anisotropic grids may be used. Other formats may be used, such as the data representing locations in a polar coordinate format. For each voxel or location, a scan response is provided by a scalar value (e.g., 16-bit dynamic range), but other representations may be used, such as RGBα values.

Given the number of different types of medical imaging systems 12, different workflows, different clinical applications, and use for diagnosis or treatment, there is a large variety in the voxel data and characteristics of the voxel data in medical imaging. Any one or more sets of voxel data representing intensity of return as a measurement of density, attenuation, elasticity, motion, uptake, temperature, molecular spin response, acoustic reflectivity, other characteristics, or combinations thereof may be acquired by the medical imaging system 22.

The renderer 24 is a general processor, central processing unit, control processor, graphics processor, digital signal processor, three-dimensional rendering processor, image processor, application specific integrated circuit (ASIC), field programmable gate array (FPGA), digital circuit, analog circuit, combinations thereof, or other now known or later developed device for rendering an image from data. The renderer 24 is a single device or multiple devices operating in serial, parallel, or separately. The renderer 24 may be a main processor of a computer, such as a laptop or desktop computer, or may be a processor for handling some tasks in a larger system, such as in the imaging system 22. The renderer 24 is configured by hardware, firmware, and/or software.

In one embodiment, the renderer 24 is a graphics processing unit (GPU) or a graphics card with rendering code. A set of graphics cards may be used. A GPU is a massively parallel computation device. CUDA or OpenCL languages are used to program the GPU. One side effect of the ray-tracing pipeline is that the computations are generally performed per pixel in screen space, allowing for efficient scaling with multiple computational devices. Multiple GPUs in a render node, GPU clusters, CPU/GPU hybrid systems, or other computational architectures may be used. Sample-based, tile-based, or frame-based distribution of the rendering may be used.

The renderer 24 includes or is a quantum computer 26. The quantum computer 26 may be a separate device that interoperates with other components of the renderer 24, such as through one or more interfaces between the quantum computer 26 and binary devices (e.g., GPU). Alternatively, the quantum computer 26 is the renderer with interfaces for operating with the medical imaging system 22, memory 28, and/or display 29.

The quantum computer 26 is a quantum circuit or other quantum computation device using qubits for superposition and measurement to collapse the state of the qubits. The quantum computer 26 is programmable with a quantum algorithm and/or forms the quantum algorithm, such as a circuit arrangement of quantum logic gates. In one embodiment, the quantum computer is an NISQ device or another probabilistic computer.

The quantum computer 26 is configured by the quantum algorithm and/or design to contribute to the rendering of a 2D image of the internal region of a patient from 3D voxel data by quantum computation. For example, a quantum search is performed to identify voxels along rays and/or to identify minimum or maximum intensities of voxels along rays. As another example, a quantum image rotation is performed to align the voxel data to an imaging plane. Other rendering operations may be performed by the quantum computer. The quantum computer 26 alone or in coordination with the renderer 24 renders the image, such as a MIP or MinIP image.

The renderer 24, using the quantum computer, generates an image or sequence of images representing the internal region of the patient. A given image represents the internal region at a specific time or period. The generated images are scalar values to be mapped to color or grayscale or are display color values (e.g., RGB) for pixels of the images. The images are output by transfer or loading into a display buffer.

The display 29 is configured to display the image output by the renderer 24. The display 29 is a monitor, LCD, projector, plasma display, CRT, printer, or other now known or later developed devise for outputting visual information. The display 29 is configured by receiving images, graphics, or other information from the renderer 24, memory 28, quantum computer 26, and/or medical imaging system 22.

The display 29 receives the image rendered from the volume scan. The image is output to the user for viewing from the screen of the display 29. In one embodiment, the image changes over time, such as due to user interaction or on-going acquisition of medical scan data.

The memory 28 is a graphics processing memory, video random access memory, random access memory, system memory, cache memory, hard drive, optical media, magnetic media, flash drive, buffer, database, combinations thereof, or other now known or later developed memory device for storing data. The memory 28 is part of the medical imaging system 22, part of a computer associated with the renderer 24, part of a database, part of another system, or a standalone device. In one embodiment, the memory 28 includes quantum logic gates or other physical instantiations of qubits.

The medical scan data, reconstructions, voxel data, frames, rendering, state information, identified voxels, counts, shear information, minimums, maximums, and/or images are stored. Any data used for imaging or data in beginning, intermediate, or final stages of processing are stored for access by the renderer 24 and/or quantum computer 26.

The memory 28 or other memory is a non-transitory computer readable storage medium storing data representing instructions executable by the programmed renderer 24 or quantum computer 26 for rendering in medical imaging. The instructions for implementing the processes, methods, and/or techniques discussed herein are provided on computer-readable storage media or memories, such as a cache, buffer, RAM, removable media, hard drive, or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for volume rendering in medical imaging, the method comprising:
   scanning a volume of a patient with a medical scanner, the scanning providing intensities representing the volume;
   creating uniform superposition states representing positions of the intensities for the volume;
   counting, by quantum amplitude amplification and estimation, voxels intersecting a ray from a pixel;

identifying, by quantum searching, the voxels intersecting the ray based on solutions initialized by the counting;

creating a superposition of the intensities of the identified voxels;

determining, by quantum finding, the minimum or maximum of the intensities of the identified voxels;

rendering the maximum or minimum intensity projection of the intensities representing the volume to a plane;

displaying an image of the maximum or minimum intensity projection, the image representing the patient.

2. The method of claim 1 wherein scanning comprises scanning with computed tomography, positron emission tomography, single photon emission computed tomography, x-rays, magnetic resonance, or ultrasound.

3. The method of claim 1 wherein scanning the volume comprises obtaining the intensities representing a three-dimensional distribution of locations in the volume, and wherein rendering comprises rendering to the image as a two-dimensional distribution of pixels from the three-dimensional distribution.

4. The method of claim 1 wherein rendering by the quantum computer comprises rendering with the quantum computation as a quantum algorithm using qubits with initialized values and measurement of a collapsed state of the qubits of the quantum computer.

5. The method of claim 1 wherein rendering comprises rendering the maximum intensity projection as pixels values each being a maximum along a ray from the pixel.

6. The method of claim 1 wherein rendering comprises rendering the minimum intensity projection as pixels values each being a minimum along a ray from the pixel.

7. The method of claim 1 wherein rendering with the quantum computation comprises rendering with a quantum search algorithm.

8. The method of claim 7 wherein rendering with the quantum search algorithm comprises searching for intensities representing the volume along each of different lines.

9. The method of claim 7 wherein rendering with the quantum search algorithm comprises searching for a minimum or maximum of the intensities representing the volume along each of different lines.

10. The method of claim 1 wherein rendering comprises rendering with a complexity of $O(\sqrt{N})$ per pixel where N is a number of voxels in the volume.

11. The method of claim 1 wherein rendering comprises rotating, by the quantum computation, slices of the intensities representing the volume to be parallel with an image plane.

12. The method of claim 11 wherein rendering further comprises determining a maximum or minimum one of the intensities for each pixel of the image plane by comparison of the intensities of each rotated slice to buffered pixel values.

13. The method of claim 12 wherein rendering comprises rendering with a complexity of $O(N*lnM*lnP)$ where N, M, and P are numbers of voxels along each spatial dimension of the volume.

14. A method for volume rendering in medical imaging, the method comprising:

acquiring medical scan data representing a volume of a patient, the medical scan data providing intensities representing the volume;

counting, by a quantum computer, a number of the intensities along a ray in the volume;

identifying, by the quantum computer, the intensities along the ray;

determining, by the quantum computer, a pixel value from the intensities along the ray;

generating, by the quantum computer, an image of the patient from the pixel values; and displaying the volume rendered image of the patient.

15. The method of claim 14 wherein volume rendering comprises rendering a minimum or maximum intensity projection as the image.

16. The method of claim 14 wherein volume rendering comprises rotating slices of the intensities of the volume with the quantum computation.

17. A system for volume rendering in medical imaging, the system comprising:

a medical imaging system configured to scan an internal region of a patient and generate voxel data representing a volume comprising the internal region;

a quantum computer configured to create uniform superposition states representing positions of the intensities for the volume; count, by quantum amplitude amplification and estimation, voxels intersecting a ray from a pixel; identify, by quantum searching, the voxels intersecting the ray based on solutions initialized by the counting, wherein the quantum searching uses a regular grid that is rotated by quantum computation using an arbitrary angle through a plurality of shear transformations; create a superposition of the intensities of the identified voxels; determine, by quantum finding, the minimum or maximum of the intensities of the identified voxels; and render the maximum or minimum intensity projection of the intensities representing the volume to an image; and a display configured to display the rendered image of the internal region.

18. The system of claim 17 wherein the quantum computer is configured to render the image as a minimum or maximum intensity projection.

* * * * *